(12) United States Patent
Seguin

(10) Patent No.: US 6,689,164 B1
(45) Date of Patent: Feb. 10, 2004

(54) ANNULOPLASTY DEVICE FOR USE IN MINIMALLY INVASIVE PROCEDURE

(75) Inventor: Jacques Seguin, 18 rue Montalivet, F-75008 Paris (FR)

(73) Assignee: Jacques Seguin, Paris (FR)

( * ) Notice: Subject to any disclaimer, the term of this patent is extended or adjusted under 35 U.S.C. 154(b) by 0 days.

(21) Appl. No.: 10/110,042

(22) PCT Filed: Oct. 10, 2000

(86) PCT No.: PCT/FR00/02814

§ 371 (c)(1),
(2), (4) Date: May 2, 2002

(87) PCT Pub. No.: WO01/26586

PCT Pub. Date: Apr. 19, 2001

(30) Foreign Application Priority Data

Oct. 12, 1999 (FR) .............................................. 99 12976

(51) Int. Cl.$^7$ ................................................. A61F 2/24
(52) U.S. Cl. .................... 623/2.36; 623/2.11; 623/2.38; 606/99
(58) Field of Search ................................ 623/2.1, 2.11, 623/2.36, 2.37, 2.38; 606/99, 100, 108, 104, 113, 232

(56) References Cited

U.S. PATENT DOCUMENTS 4,042,979 A * 8/1977 Angell ....................... 623/2.37
5,716,397 A * 2/1998 Myers ........................ 623/2.36

* cited by examiner

*Primary Examiner*—Corrine McDermott
*Assistant Examiner*—Kamrin R Landrem
(74) *Attorney, Agent, or Firm*—Oliff & Berridge, PLC

(57) ABSTRACT

A device, particularly useful for reconstructing heart valves, that includes:

an implant having an elongate, deformable structure so that it can assume an elongate shape for insertion into the body of the patient through a small-diameter passage, approximately 1 to 2 cm, and a curved shape adapted for creating the annuloplasty, and a tubular instrument able to receive the implant at least partially within itself, which is sufficiently rigid to allow insertion of the implant into the body of the patient through the passage; this instrument has an opening at its distal part enabling access to implant, means for rotationally locking the implant relative thereto, means for holding implant relative thereto, and means for detecting its angular orientation inside the body of the patient.

14 Claims, 4 Drawing Sheets

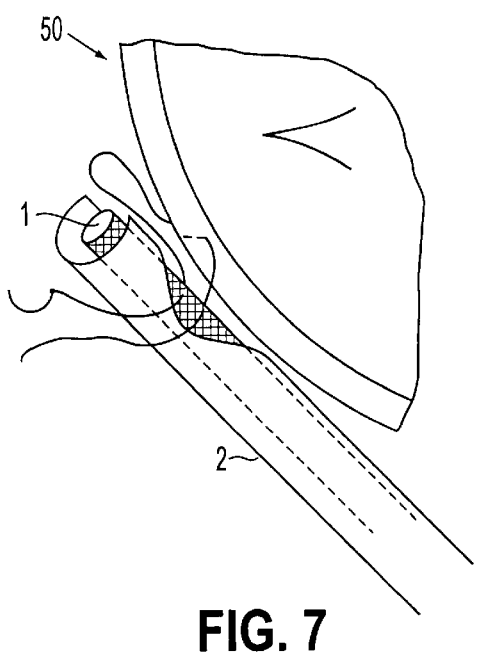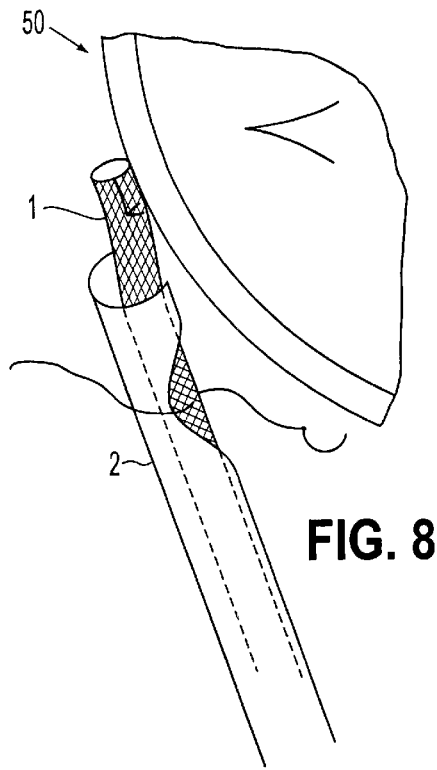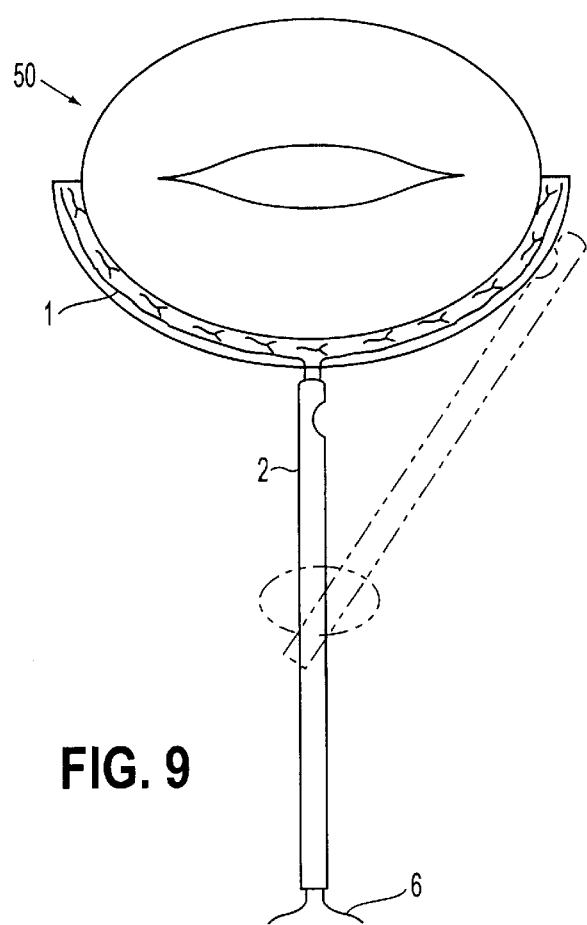

ANNULOPLASTY DEVICE FOR USE IN MINIMALLY INVASIVE PROCEDURE

BACKGROUND OF THE INVENTION

1. Field of the Invention

The present invention relates to an annuloplasty device that can be used by a minimally invasive route, particularly forrconstruction of heart valves.

2. Description of Related Art

In a normal heart valve, thee valves overlap at the center of the fibromuscular ring surrounding the valve, thus making the valve impermeable to regurgitation of blood.

A number of pathological conditions may cause this fibromuscular ring to deform or dilate, so that the valves are no longer impermeable.

It is then necessary to "reconstruct" the valve by placement of an implant that restores a correct shape and/or section to the fibromuscular ring; this operation is normally known as "annuloplasty."

Such an implant has, in a manner known of itself, an annular shape and is sutured to the fibromuscular ring. It may have a rigid, semi-rigid, or flexible structure.

Insertion and placement of this type of implant requires an invasive approach, making these operations length, complex, and delicate.

Minimally invasive surgery reduces the surgical burden by reducing the approach to one or more incisions 1 to 3 cm in diameter. However, this surgery is not currently usable for annuloplasty as the valve reconstruction ring cannot pass through such openings, particularly if it is rigid or semi-rigid. Moreover, such a ring and the instrument for inserting this ring would be very difficult to manipulate, and engagement of suture threads in the ring once it had been placed in the heart would be problematic.

SUMMARY OF THE INVENTION

The goal of the present invention is to overcome these fundamental drawbacks.

Its main objective is to provide a device for minimally invasive annuloplasty, i.e. with one or more approaches formed by passages approximately 1 to 2 cm in diameter.

Another goal of the invention is to provide a device to facilitate suturing of the ring at the treatment site.

The device in question comprises, in a manner known of itself, an implant shaped so that it can be sutured to tissues in order to create the annuloplasty.

According to the invention:

the implant has an elongate, deformable the implant has an elongate, deformable structure so that it can assume an elongates shape for insertion into the body of the patient through a small-diameter passage, approximately 1 to 2 cm in diameter, and a curved shape adapted for creating the annuloplasty, and the device has a tubular instrument able to receive said implant at least partially within itself, which is sufficiently rigid to allow insertion of the implant into the body of the patient through said passage; this instrument has an opening at its distal part enabling access to the implant and comprises means for rotationally locking the implant relative thereto, means for holding the implant relative thereto, and means for detecting its angular orientation inside the body of the patient.

By adequate orientation of the instrument relative to said tissues, the locking and detecting means enable the implant to be adequately positioned relative to these tissues to create the annuloplasty because of said curved shape of the implant; these locking means and the holding means hold a portion of the implant in an adequate position relative to the tissues when the thread for suturing this portion to these tissues is positioned, then releases this portion of the implant once it has been sutured to the tissues.

In practice, a trocar containing a tube is inserted until the distal part of this trocar, and of this tube, are near the site to be treated; the trocar is withdrawn and the tube then allows the instrument inside which the implant is held to be inserted; the distal part of the implant, accessible at the distal part of the instrument, is attached to the tissues by a first suture stitch; an additional portion of the implant is then dispensed by the instrument, then this portion if attached to the implant by a second suture stitch; a further portion of the implant is then released then sutured, and so forth until the entire implant is attached to the tissues.

The implant may have an elastic structure and have the aforementioned curved shape in the non-deformed state of this structure; this implant would then be deformed elastically when it was engaged in the instrument then resume its curved shape as it was dispensed by the instrument; the locking and detecting means of the instrument would then hold the implant during suturing so that the concave part of the implant was located radially inward of the annuloplasty to be created.

The implant could also be made of a shape-memory alloy such as a nickel-titanium alloy known as Nitinol.

Preferably, however, the implant has a body with a flexible non-elastic structure, and at least one cord connected to said body in the vicinity of one end of the latter; each cord extends over one lengthwise side of this body up to a location remote from said end, is slidably mounted relative to this body and relative to said location, and has a length such that traction may be exerted thereon once the body has been sutured to said tissues; the whole is shaped such that traction can be exerted on each cord to reduce the length of said body by puckering said structure so as to reduce the circumference of the implant and hence create the annuloplasty.

In this case, the detecting means enable the implant to be held in a position wherein each cord is positioned non the radially inner side of the body at the time the implant is being sutured.

Once the implant has been sutured, traction is exerted on the cord or cords so as to pucker and hence stiffen said body, then this cord or these cords are sutured so that they can be kept under tension.

According to one possible embodiment of the invention, in this case said body is comprised of a braid of textile material, with each cord passing inside this braid.

The implant may have a single cord connected to one end of the body and exiting in the vicinity of the other end thereof; preferably, however, the implant has two cords, one of which is connected to one end of the body and the other to the other end of this body, and the two cords each extend substantially over half of the body, up to locations that are near each other and essentially in the median area of this body.

According to one possible embodiment of the invention, the instrument has a lateral notch in the vicinity of its distal end that communicates via a slot with a distal opening in this instrument the depth of said notch being such as to uncover the lengthwise side of the body that is destined, after the suturing, to be located radially outside the annuloplasty to be created, but such that it covers the lengthwise side of body destined to be located on the radially inner side of this annuloplasty, namely on the side on which the cord or cords are located.

This notch enables only the part of the body that is to be sutured to the tissues to be uncovered, and eliminates any risk of the cord or cords being caught by the suture needle.] preferably, holding means such as the foregoing are located on either side of this notch to fully stiffen the implant at the notch and thus facilitate passage of the suture thread.

The instrument may then have two tubular parts of which the first is engaged in the second; said first tubular part has teeth at its distal end that are movable radially between a normal radially outer position in which they allow the implant to slide and a radially inner position in which they grip the implant between them and prevent this sliding, said teeth being shaped such that their radially outer faces project, in said normal position, beyond the outer face of said first tubular part; the second tubular part) can slide axially relative to the first tubular part between a retracted position in which it does not abut said radially outer faces of the teeth, and an active position in which it abuts these radially outer faces, and moves the teeth into their radially inner position.

According to a second possible embodiment of the invention, the implant body has, viewed transversally, a tubular part and a flat part extending radially relative to said tubular part°; the instrument has a tubular part that has a lateral slot provided in its distal part, and has a rod that can be engaged in this tubular part; said tubular part of the body of the implant is engaged inside said tubular part of the instrument and receives said rod therein while said flat part passes through said slot and extends outside said tubular part of the instrument.

This slot and this rod constitute said means that lock and hold the implant in the instrument. The implant is released simply by withdrawing the rod as the portions of the implant attached to the tissues to enable the tubular part of the implant body to pass through said slot.

The instrument can have two tubular parts, namely the aforementioned tubular part and an outer tubular part in which the aforesaid tubular part is engaged, and the implant is placed therein.

Advantageously, the position of said flat part of the implant body extending beyond the instrument has means for attaching the implant to the tissues, which are pre-positioned on said part.

These means are in particular comprised of suture threads.

This pre-positioning of said attaching means, made possible by the existence of said flat part, considerably facilitate the attaching of the implant to the tissues.

Preferably, in this case, the attaching means are comprised of suture threads and, opposite each suture thread, the implant has at least one reel mounted thereon, on? Which the suture thread is wound. The suture needle connected to this thread can also be held on this reel for as long as it is in use.

When the suture threads traverse said flat part, and hence form two strands each that extend on either side of this flat part, the instrument advantageously has one reel on each of these sides located on either side of said flat part, with each of the reels receiving one of the two strands of suture thread.

BRIEF DESCRIPTION OF THE DRAWINGS

For intelligibility, the invention is described once again below with reference to the attached schematic drawing showing, as nonlimiting examples, two possible embodiments of the annuloplasty device to which it relates.

FIGS. 5 to 8 are enlarged and highly simplified views of this heart valve and this implant and instrument, during four successive stages of positioning a suture stitch of the implant at a valve tissue;

FIG. 9 is a view similar to FIG. 4 once the implant has been positioned and before the valve annuloplasty is created;

DETAILED DESCRIPTION OF PREFERRED EMBODIMENTS

Figure 1:
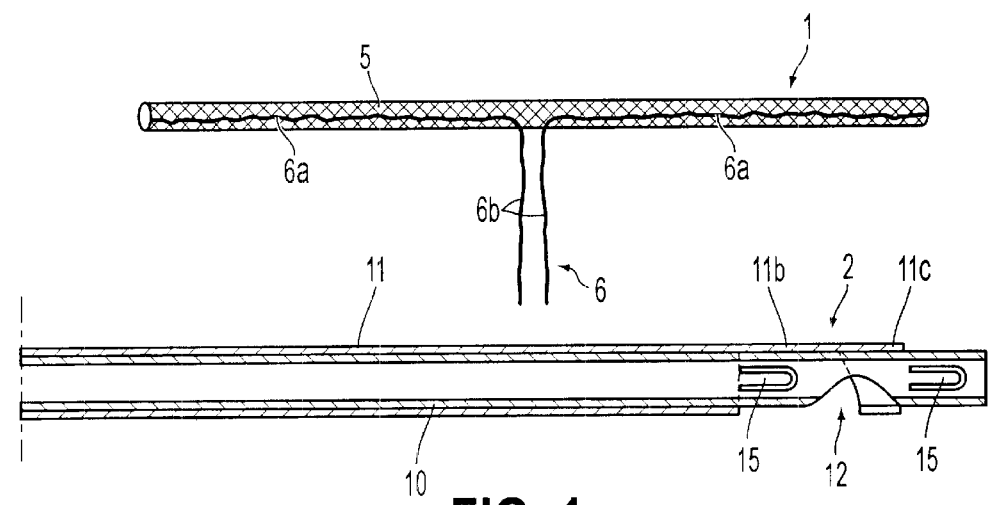
FIG. 1 is a side view of an implant and a tubular instrument of which this device is comprised, according to a first embodiment.

FIG. 1 represents an implant 1 enabling an annuloplasty to be created on a heart valve and a tubular instrument 2 enabling said implant 1 to be positioned.

Implant 1 comprises a body 5 composed of a tubular braid made of textile material, for example a polyester, and by two cords 6.

The ends of body 5 are tied to keep the strands of the braid together.

One of the ends of a cord 6 is connected, by said tie, to one of the ends of the braid while the end of the other cord 6 is connected, by the other tie, to the other end of the same braid. These two cords 6 each have a part 6a extending inside body 5, along one lengthwise side thereof, up to near the median portion of this body 5, and a portion 6b which extends beyond this body 5, each cord 6 passing through this body 5 and exiting therefrom at said median portion. The two cords 6 can slide inside the braid and through the openings through which they pass through this braid.

The length of these cords 6 is such that each of cords 6 extends outside the body of the patient when implant 1 is attached to the valve, as will be described below.

Instrument 2 has two tubular parts 10, 11 engaging each other.

Radially inner part 10 has a lateral notch 12 in the vicinity of its distal end, which communicates with distal opening 13 of this part via a slot 14. The width of this slot 14 is such that a suture stitch enabling body 5 to be attached to the heart valve can pass through it. The depth of notch 12 is such that this notch uncovers the lengthwise side of body 5 opposite the side where cords 6 are located when these cords are under tension but such that the notch covers this lengthwise side on which said cords 6 are located.

This part 10 also has two pairs of teeth 15, each pair being located lengthwise on one side of notch 12. Part 10 is made of a moldable synthetic material having some degree of flexibility, and each tooth 15 is made of the same material as this part 10, by molding, being separated from part 10 by a U-shaped slot. Teeth 15 of each pair of teeth are diametrically opposite each other and each tooth 15 has a part 16 resting against implant 1, projecting radially inside part 10.

Figure 3:
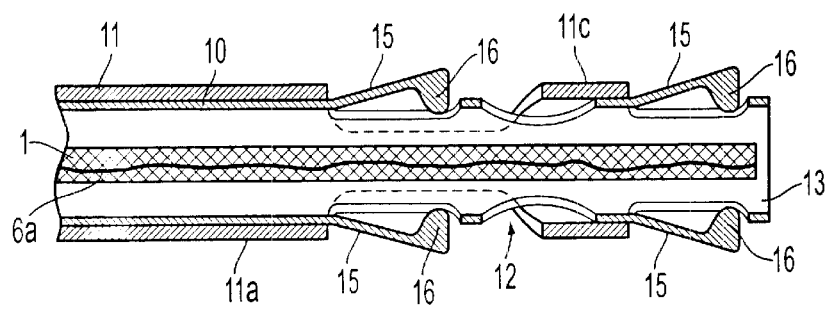
FIG. 3 is a side view of this implant and this instrument, in lengthwise section.

Each tooth 15 normally occupies the position drawn in solid lines in FIG. 3, in which it is inclined outside part 10 such that its abutting part 16 is located at a distance from body 5 of implant 1.

This same figure shows that the flexibility of the material of which part 10 is made enables these teeth 15 to flex into a radially inner position in which parts 16 grip the implant 1 between them. This grip squeezes body 5, immobilizing it relative to instrument 2 both rotationally and slidably with respect thereto. This grip also enables cords 6 to be kept slightly under tension so that they are held along the aforesaid lengthwise side of this body 5.

Figure 2:
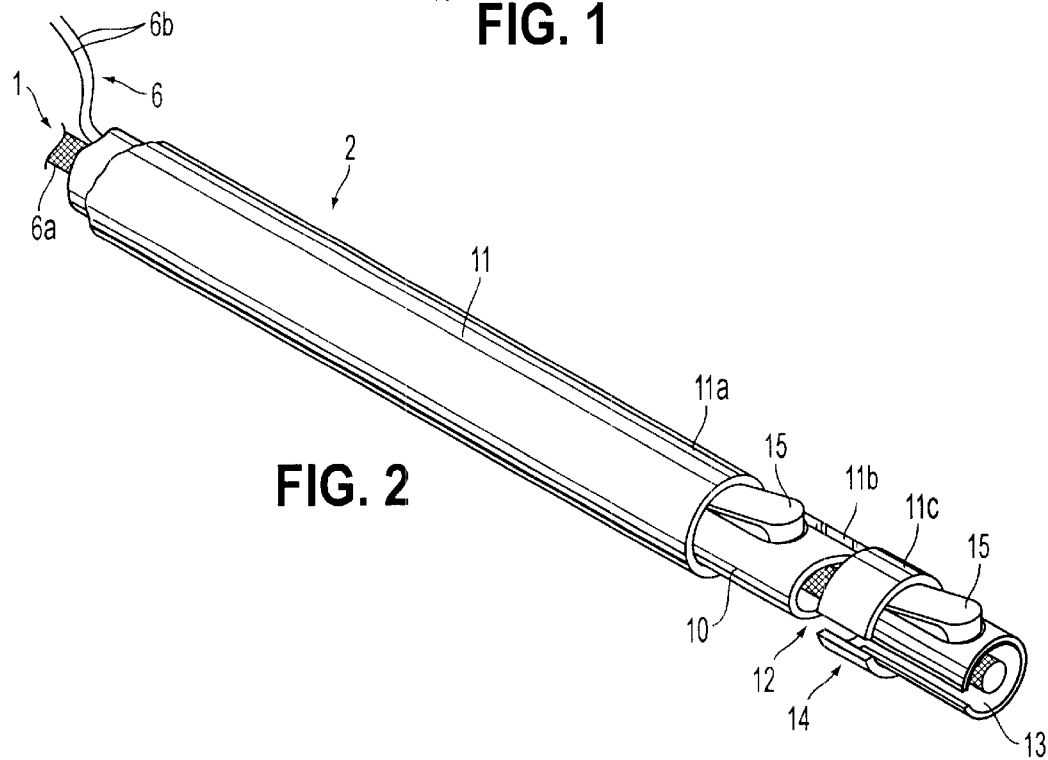
FIG. 2 is a perspective view of this implant and this instrument, the implant being located outside the instrument.

Part 11 is engaged on part 10 and can slide axially relative thereto. It has a proximal tubular part 11a, an intermediate part 11b, and a distal tubular part 11c which is slotted lengthwise. FIGS. 2 and 3 show that parts 11a and 11c are able, in a first axial position relative to part 10, to cover proximal and distal teeth 15 respectively so as to move these teeth 15 into the aforesaid radially inner position and, in the axial position shown, to be positioned outside these teeth 15 such that they occupy their normal radially outer position.

Part 11b has a length such that part 11c is completely unable to cover notch 12 in this position.

Moreover, part 11 is rotationally locked relative to part 10, for example by projections sliding in grooves, such that the slot of part 11c coincides with slot 14.

Proximally, instrument 2 has a mark showing the side of this instrument where notch 12 is located and enabling this instrument 12 to be oriented angularly.

In practice, implant 1 is placed in instrument 2 such that the distal part of implant 1 is at the distal opening 13 of the instrument and cords 6 extend along the side of part 10 opposite the side on which notch 12 opens to the outside. Part 11 is then moved relative to part 10, which brings teeth 15 to their radially inner position and thus immobilizes implant 1 relative to instrument 2 both axially and rotationally while keeping body 5 tensioned in notch 12.

In order to position implant 1, an incision is made at an appropriate point in the rib cage of the patient, then a trocar containing a tube is inserted under the skin of the patient and through the fat and tissues up to the approaches to the heart valve to be treated.

Figure 4:
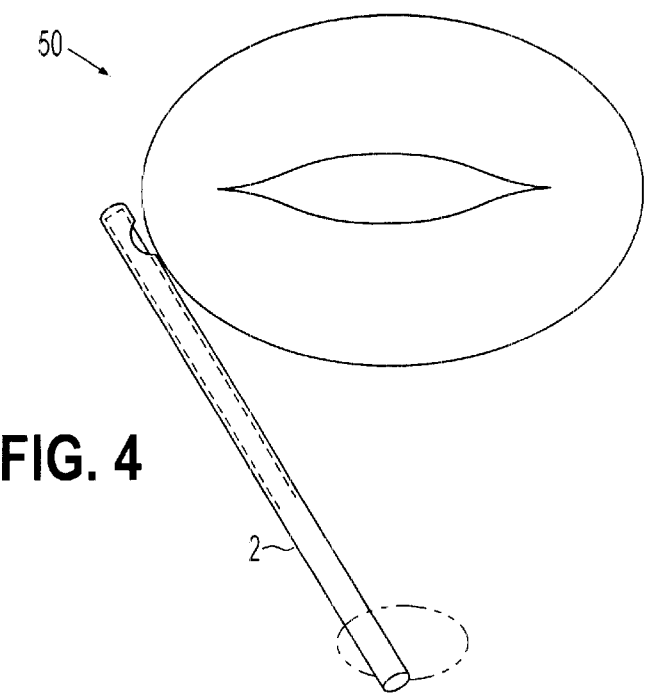
FIG. 4 is a highly simplified view of a heart valve on which an annuloplasty is to be done, as well as said implant and instrument.

The trocar is then withdrawn and the implant 1 together with instrument 2 are engaged in the body of the patient by means of said tube, then properly oriented by means of the aforesaid proximal mark (FIG. 4).

Figure 5:
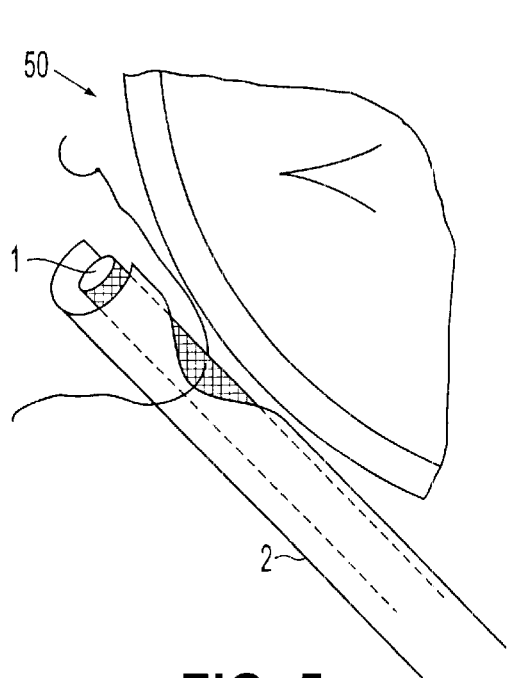
Figure 6:
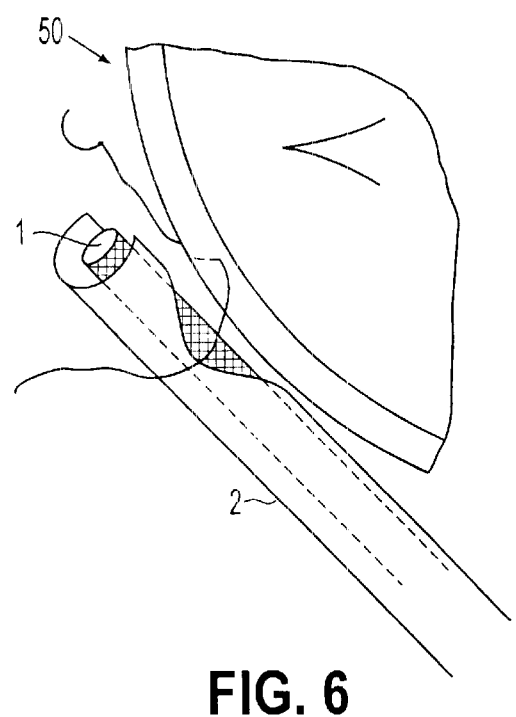

As shown in FIGS. 5 to 7, the suture thread is successively passed into implant 1 at notch 12 (FIG. 5) then into the fibromuscular ring surrounding valve 50 to be treated (FIG. 6) then again in implant 1 at the notch 12 (FIG. 7). Part 11 is then retracted relative to part 10 to allow implant 1 to slide in order to dispense an additional portion of this implant 1. The suture thread is then knotted to attach the implant to the fibromuscular ring.

Part 11 is then advanced again to immobilize implant 1 in instrument 2, then a suture thread is again passed into implant 1 at notch 12 (FIG. 8) and into the fibromuscular ring; the implant is again allowed to slide for this suture thread to be knotted and an additional portion of implant 1 to be dispensed.

These steps are repeated as often as necessary to attach the entire implant 1 around all or part of valve 50.

Once implant 1 has been attached to the fibromuscular ring, traction is exerted on cords 6 to reduce the length of body 5, puckering its structure, to reduce the circumference of implant 1 and thus create the annuloplasty; the cords 6 are then knotted to each other and a knot pusher is used to bring the knot to body 5 so that cords 6 are kept under tension.

Figure 10:
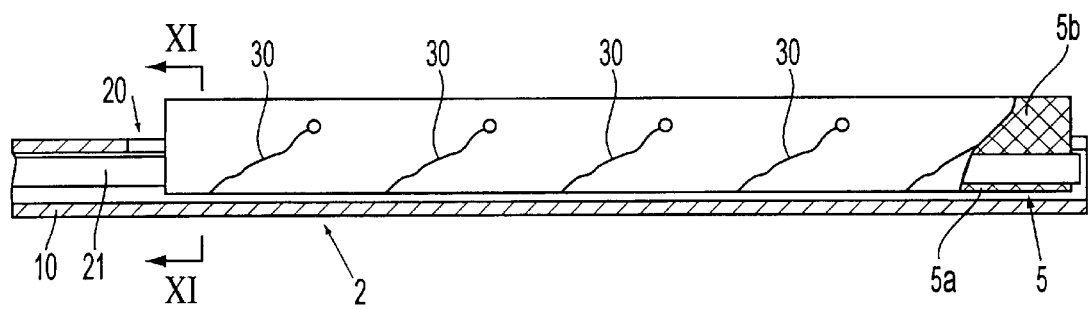
FIG. 10 is a side view, with a partial section of an implant and part of an instrument of which this device is comprised, according to a second embodiment.
Figure 11:
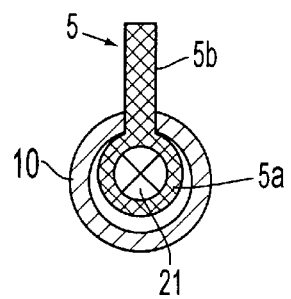
FIG. 11 is a sectional view along line XI—XI in FIG. 10.
Figure 12:
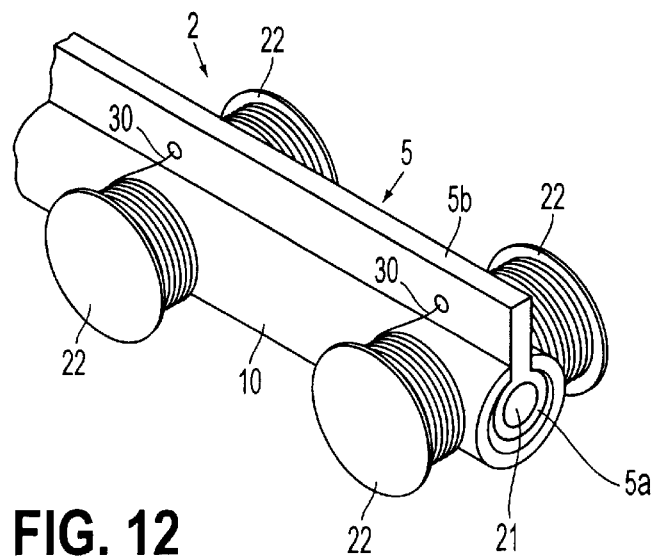
FIG. 12 is a partial perspective view of an implant and a part of the instrument according to this second embodiment, the implant being equipped with reels.

FIGS. 10 to 12 show an implant whose body 5 is also comprised of a textile braid and is equipped with two stiffening cords as above, not shown.

As shown in these figures, body 5, seen in cross section, has a tubular part 5a and a flat part 5b extending radially relative to this tubular part 5a. Flat part 5b is traversed by a plurality of suture threads 30 lined up with each other, to the ends of which the suture needles are crimped.

Instrument 2 has an inner tubular part 10 with a lateral slot 20 provided in its distal part, and has a rod 21 that can be engaged in part 10, said rod 21 having a larger diameter than the width of slot 20.

It appears that part 5a of the implant is engaged inside part 10 and receives rod 21 within itself while part 5b passes through slot 20 arriving at the outside of part 10.

Instrument 2 also has an outer tubular part (not shown) in which tubular part 10 and the implant placed therein engage.

Slot 20 and rod 21 constitute means for locking and holding implant 1 in instrument 2. Implant 1 is simply released by pulling out said outer tubular part, then withdrawing rod 21 as the portions of implant 1 become attached to the tissues, to enable part 5a to pass through slot 20.

Thus, as shown in FIG. 12, opposite each suture thread 30, on each of the sides of part 10 located on either side of part 5b, two reels 22 can be mounted on implant 2. Each strand of a suture thread 30 is intended to be wound onto reel 22 located on the same side as itself and the suture needle is intended to be held on this reel 22 for as long as it is in use. Each reel 22 can have a circular shape or an oval shape adapted to receive needle 31.

The invention thus provides an annuloplasty device usable by a minimally invasive route, particularly for reconstruction of heart valves, so that a relatively noninvasive annuloplasty can be created through one or more approaches formed by passages approximately 1 to 2 cm in diameter.

It goes without saying that the invention is not confined to the embodiment described above as an example but on the contrary covers all alternative embodiments. Thus, the implant could have an elastic structure and have the aforesaid curved shape in the non-deformed state of this structure, or be made of a shape-memory alloy such as a nickel-titanium alloy known as Nitinol.

What is claimed is:

1. Annuloplasty device usable by a minimally invasive route, in particular for heart valve reconstruction, comprising an implant shaped to be suturable to tissues in order to create the annuloplasty; characterized in that the implant has an elongate, deformable structure so that it can assume an elongate shape for insertion into the body of the patient through a small-diameter passage, approximately 1 to 2 cm in diameter, and a curved shape adapted for creating the annuloplasty, and the device has a tubular instrument able to receive said implant at least partially within itself, which is sufficiently rigid to allow insertion of implant into the body of the patient through said passage; this instrument has an opening at its distal part enabling access to implant and comprises means for rotationally locking the implant relative thereto, means for holding implant relative thereto, and means for detecting its angular orientation inside the body of the patient.

2. Device according to claim 1, characterized in that implant has an implant body with a non-elastic flexible structure, and at least one cord connected to said implant body in the vicinity of one end of the latter; said at least one cord extends over one lengthwise side of said implant body up to a location remote from said end, is slidably mounted relative to said implant body and relative to said location, and has a length such that traction may be exerted thereon once said implant body has been sutured to said tissues; the device is shaped such that traction can be exerted on said at least one cord to reduce the length of said implant body by puckering said structure so as to reduce the circumference of implant and hence create the annuloplasty.

3. Device according to claim 2, characterized in that said implant body is comprised of a braid of textile material and in that said at least one cord passes inside this braid.

4. Device according to claim 2, characterized in that the implant has two cords one of which is connected to one end of said implant body and the other to the other end of said implant body and in that the two cords each extend over substantially half of said implant body up to locations near each other substantially in the median area of said implant body.

5. Device according to claim 2, characterized in that the instrument has a lateral notch in the vicinity of its distal end that communicates via a slot with a distal opening in this instrument, the depth of said notch being such as to uncover the lengthwise side of said implant body that is destined, after the suturing, to be located radially outside the annuloplasty to be created, but such that it covers the lengthwise side of said implant body destined to be located on the radially inner side of this annuloplasty, namely on the side on which the at least one cord is located.

6. Device according to claim 5, characterized in that the holding means referred to above are located on either side of notch.

7. Device according to claim 5, characterized in that the instrument has two tubular parts of which the first is engaged in the second; said first tubular part has teeth at its distal end that are movable radially between a normal radially outer position in which they allow implant to slide and a radially inner position in which they grip the implant between them and prevent this sliding, said teeth being shaped such that their radially outer faces project, in said normal position, beyond the outer face of said first tubular part; the second tubular part can slide axially relative to the first tubular part between a retracted position in which it does not abut said radially outer faces of the teeth, and an active position in which it abuts these radially outer faces, and moves the teeth into their radially inner position.

8. Device according to claim 1, characterized in that the implant body has, viewed transversally, a tubular part and a flat part extending radially relative to said tubular part; the instrument has a tubular part that has a lateral slot provided in its distal part, and has a rod that can be engaged in this tubular part; said tubular part of the implant body is engaged inside said tubular part of instrument and receives said rod therein while said flat part passes through said slot and extends outside said tubular part of the instrument.

9. Device according to claim 8, characterized in that the instrument has two tubular parts, namely the tubular part referred to above and an outer tubular part in which the aforesaid tubular part and the implant placed therein are engaged.

10. Device according to claim 8, characterized in that the portion of said flat part of the implant body extending beyond instrument has means for attaching the implant to the tissues, which are pre-positioned on said flat part.

11. Device according to claim 8, characterized in that the attaching means are comprised of suture threads and in that the implant has, opposite each suture thread, at least one reel mounted thereon, onto which suture thread is wound.

12. Device according to claim 11, characterized in that the suture threads pass through said flat part and in that the instrument has a reel on each of its sides located on either side of said flat part, each of reels receiving one of the two strands of suture thread.

13. Device according to claim 1, characterized in that the implant has an elastic structure and has the aforementioned curved shape in the non-deformed state of this structure, this implant being deformed elastically when it is engaged in the instrument, then returns to its curved shape as it is dispensed by the instrument.

14. Device according to claim 1, characterized in that the implant is made of a shape-memory alloy such as a nickel-titanium alloy known as Nitinol.

* * * * *